United States Patent
Salcin et al.

(10) Patent No.: US 9,574,992 B1
(45) Date of Patent: Feb. 21, 2017

(54) SINGLE WAVELENGTH ELLIPSOMETRY WITH IMPROVED SPOT SIZE CAPABILITY

(71) Applicant: KLA-Tencor Corporation, Milpitas, CA (US)

(72) Inventors: Esen Salcin, Milpitas, CA (US);
Fuming Wang, Santa Clara, CA (US);
Kevin Peterlinz, San Ramon, CA (US);
Hidong Kwak, San Jose, CA (US);
Damon Kvamme, Los Gatos, CA (US);
Uri Greenberg, San Jose, CA (US);
Daniel R. Hennigan, Livermore, CA (US)

(73) Assignee: KLA-Tencor Corporation, Milpitas, CA (US)

(*) Notice: Subject to any disclaimer, the term of this patent is extended or adjusted under 35 U.S.C. 154(b) by 0 days.

(21) Appl. No.: 15/214,814

(22) Filed: Jul. 20, 2016

Related U.S. Application Data

(60) Provisional application No. 62/286,279, filed on Jan. 22, 2016.

(51) Int. Cl.
| | | |
|---|---|---|
| *G01J 4/00* | (2006.01) | |
| *G01N 21/21* | (2006.01) | |
| *G01J 4/04* | (2006.01) | |

(52) U.S. Cl.
CPC ............. *G01N 21/211* (2013.01); *G01J 4/04* (2013.01); *G01N 2201/0683* (2013.01); *G01N 2201/12* (2013.01)

(58) Field of Classification Search
CPC ....................................... G01J 4/00; G01J 4/04
(Continued)

(56) References Cited

U.S. PATENT DOCUMENTS

| | | |
|---|---|---|
| 5,608,526 A | 3/1997 | Piwonka-Corle et al. |
| 5,859,424 A | 1/1999 | Norton et al. |

(Continued)

OTHER PUBLICATIONS

Salcin, Esen and Codona, Johanan L., Laboratory Demonstration of an Anti-Halo Reconstructor for Closed-Loop Adaptive Halo Suppression, SPIE Astronomical Telescopes and Instrumentation, Adaptive Optics Systems II, Proc. SPIE 7736, 2010.
(Continued)

*Primary Examiner* — Roy M Punnoose
(74) *Attorney, Agent, or Firm* — Spano Law Group; Joseph S. Spano

(57) ABSTRACT

Methods and systems for performing single wavelength ellipsometry (SWE) measurements with reduced measurement spot size are presented herein. In one aspect, a pupil stop is located at or near a pupil plane in the collection optical path to reduce sensitivity to target edge diffraction effects. In another aspect, a field stop is located at or near an image plane conjugate to the wafer plane in the collection optical path to reduce sensitivity to undesired optical-structural interactions. In another aspect, a linear polarizer acting on the input beam of the SWE system includes a thin, nanoparticle based polarizer element. The nanoparticle based polarizer element improves illumination beam quality and reduces astigmatism on the wafer plane. The pupil and field stops filter out unwanted light rays before reaching the detector. As a result, measurement spot size is reduced and tool-to-tool matching performance for small measurement targets is greatly enhanced.

20 Claims, 10 Drawing Sheets

(58) Field of Classification Search
USPC .......................................................... 356/369
See application file for complete search history.

(56) References Cited

U.S. PATENT DOCUMENTS

| | | | |
|---|---|---|---|
| 6,429,943 | B1 | 8/2002 | Opsal et al. |
| 6,693,711 | B1* | 2/2004 | Leger .................... G01J 4/00 |
| | | | 356/364 |
| 6,734,968 | B1 | 5/2004 | Wang et al. |
| 7,006,222 | B2 | 2/2006 | Krishnan |
| 7,253,901 | B2 | 8/2007 | Janik et al. |
| 7,478,019 | B2 | 1/2009 | Zangooie et al. |
| 7,933,026 | B2 | 4/2011 | Opsal et al. |
| 2009/0147247 | A1* | 6/2009 | Endo .................. G03F 7/70625 |
| | | | 356/237.2 |
| 2013/0114085 | A1 | 5/2013 | Wang et al. |
| 2014/0111791 | A1 | 4/2014 | Manassen et al. |
| 2014/0172394 | A1 | 6/2014 | Kuznetsov et al. |
| 2014/0222380 | A1 | 8/2014 | Kuznetsov et al. |

OTHER PUBLICATIONS

Codona, Johanan L., Stellar coronagraphs for telescopes with arbitrary pupils, Astronomical Adaptive Optics Systems and Applications, Proc. SPIE 5169, 2003.
Losurdo, Maria and Hingerl, Kurt (Eds.), Ellipsometry at the Nanoscale, Springer-Verlag Berlin Heidelberg, 2013.
Trager, Frank (Ed.), Springer Handbook of Lasers and Optics, Springer-Verlag Berlin Heidelberg, 2012.

* cited by examiner

SINGLE WAVELENGTH ELLIPSOMETRY WITH IMPROVED SPOT SIZE CAPABILITY

CROSS REFERENCE TO RELATED APPLICATION

The present application for patent claims priority under 35 U.S.C. §119 from U.S. provisional patent application Ser. No. 62/286,279, entitled "Methods of Improved Spot Size Capability in Single Wavelength Ellipsometry," filed Jan. 22, 2016, the subject matter of which is incorporated herein by reference in its entirety.

TECHNICAL FIELD

The described embodiments relate to metrology systems and methods, and more particularly to methods and systems for improved measurement of semiconductor structures.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, composition, overlay and other parameters of nanoscale structures.

Ongoing reductions in feature size, increasing geometric complexity, and more diverse material compositions of semiconductor devices impose difficult requirements on optical metrology systems that are relied upon for process development and process monitoring. To achieve device performance requirements, the thickness and composition of the thin films (e.g., oxide, nitride, metal layers, etc.) formed on a silicon wafer must be accurately controlled during the semiconductor device manufacturing process.

Single Wavelength Ellipsometry (SWE) based measurement techniques and systems are often employed to measure thin film characteristics. SWE systems utilize model-based measurement techniques to determine physical properties of film structures based on polarization properties of light reflected from the structure under measurement. Exemplary metrology systems and techniques are described in detail in U.S. Pat. No. 6,734,968 issued on May 11, 2004, U.S. Pat. No. 7,006,222 issued on Feb. 28, 2006, and U.S. Pat. No. 7,253,901 issued on Aug. 7, 2007, all assigned to KLA-Tencor Corporation, the contents of each are incorporated herein by reference in their entirety.

In many advanced film measurement applications, SWE systems are preferred for their excellent measurement repeatability and optical stability. The single wavelength polarized light source delivers constant light output and excellent wavelength stability. SWE systems exhibit excellent tool-to-tool matching performance among multiple tools in the same, or different, fabrication facilities. This enables sharing of ellipsometry models, measurement recipes, and optical constants across multiple SWE systems.

However, the light sources employed by SWE systems exhibit large coherence lengths, for example, on the order of tens of meters. This leads to significant coherence artifacts in measurement signals that can be detrimental to system performance. Coherence based artifacts arise in many different circumstances. In one example, light diffracted from the edges of a metrology target leads to interference along the propagation path between light reflected from inside the boundary of the metrology target and light reflected from outside the metrology target. In another example, ghost images arise due to interference between even numbered reflections from surfaces of optical elements. In another example, measured data is contaminated by scattering effects from optical surface roughness and coatings, particulate contaminants, black surface treatments, and other light interactions with opto-mechanical structures.

Contaminated light does not exclusively carry information about the measurement target box. Any amount of contaminated light detected by the SWE system contributes to measurement error. The minimum target size that can be measured within a given thickness measurement error tolerance is often termed the "spot size." The measurement spot size is a function of detected, contaminated light. The larger the amount of detected contaminated light the larger "spot size" will be measured for a given thickness error criteria. In some examples, contamination light levels must be less than $10^{-5}$ of the detected light to meet the measurement error specification for a reasonable spot size. As spot size requirements and measurement error requirements continue to grow more stringent, further reductions in contamination light are needed.

Future metrology applications present challenges due to small feature size and multi-parameter correlation. Improvements to SWE systems are desired.

SUMMARY

Methods and systems for performing single wavelength ellipsometry (SWE) measurements with reduced measurement spot size are presented herein.

In one aspect, a pupil stop is located at or near a pupil plane in the collection optical path to reduce sensitivity to target edge diffraction effects. In some embodiments, a round shaped aperture is located in the beam of collected light at or near the pupil plane of the collection optics of a SWE system. In a preferred embodiment, pupil stop 120 is located in the pupil plane of the collection optics at a location where the spatial separation of the desired measurement signals from contaminated signals is at a maximum.

In another aspect, a field stop is located at or near an image plane conjugate to the wafer plane in the collection optical path to reduce sensitivity to undesired optical-structural interactions. In some embodiments, a rectangular shaped field stop is included in the collection optical path. In a preferred embodiment, the field stop is located in the image plane before the analyzer.

In another aspect, a linear polarizer acting on the input beam of the SWE system includes a thin, nanoparticle based polarizer element. The nanoparticle based polarizer element improves illumination beam quality and reduces astigmatism on the wafer plane. The thin, nanoparticle based polarizer element is located in the illumination path after the illumination source, but before the elliptical polarizer of the SWE system.

In a further aspect, the dimensions of the apertures of the field stop, pupil stop, or both, are adjusted to increase measurement sensitivity to structure specific features, such as film thickness, by limiting light transmission. By limiting light transmission, light originating outside the metrology target at the wafer plane, light associated with interference generated by the interaction between light originating inside the metrology target and light originating outside the metrology target, and stray light reflected into the collected beam is absorbed, or otherwise redirected away from the detector. As a result, measurement spot size is reduced and tool-to-tool matching performance for small measurement targets is greatly enhanced.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for performing single wavelength ellipsometry (SWE) measurements with reduced measurement spot size are presented herein. A reduction in measurement spot size is achieved by including 1) a pupil stop located in the collection optical path at a location near a pupil plane of the SWE system; 2) a field stop located in the collection optical path at a location near an image plane conjugate to the wafer plane of the SWE system; 3) a linear polarizer including a thin, high extinction ratio, nanoparticle based polarizer element located in the illumination path between the illumination source and the wafer of the SWE system; or any combination thereof. The reduction in measurement spot size enables more accurate thin film measurements and enhanced tool-to-tool matching performance. In some examples, a tool-to-tool matching specification of 0.02 Angstroms for a thin film measurement with measurement spot sizes ranging from 400 micrometers to 40 micrometers is achieved.

A single wavelength ellipsometer performs thin film measurements with improved beam quality and reduced sensitivity to target edge diffraction effects and undesired optical-structural interactions. The SWE system is configured to include any of an aperture near the collection pupil plane, an aperture near the image plane conjugate to the wafer plane, and a linear polarizer including a thin, nanoparticle based polarizer element. Each element is selected to optimize measurement sensitivity to the parameters of interest, measurement accuracy, and system matching. The nanoparticle based polarizer element improves illumination beam quality and reduces astigmatism on the wafer plane. The pupil and field apertures provide obscuration and effectively absorb unwanted, collected light diffracted or reflected from outside the measurement target before it reaches the detector. As a result, thin film measurement accuracy for small measurement targets (e.g., 40 μm×40 μm targets) is greatly enhanced.

Figure 1:
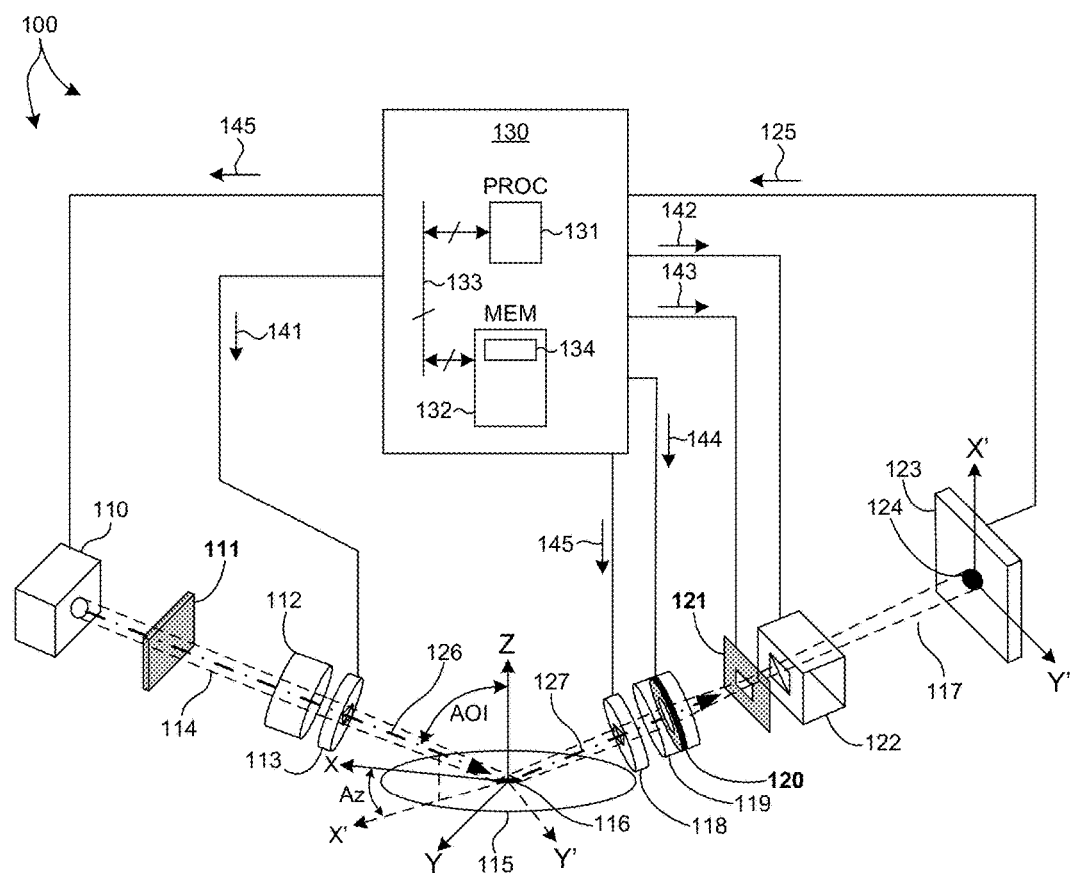
FIG. 1 depicts an exemplary SWE system 100 having reduced measurement spot size.

FIG. 1 depicts an exemplary SWE system 100 having reduced measurement spot size. SWE system 100 includes an illumination source 110 that generates a beam of illumination light 114 incident on a wafer 115. The beam of illumination light 114 passes through a linear polarizer including a thin, nanoparticle based, high extinction ratio input beam polarizer element 111, illumination optics 112, and an elliptical polarizer element 113 (e.g., a quarter waveplate compensator, phase retarder, etc.) as the beam propagates from the illumination source 110 to wafer 115. The elements between illumination source 110 and wafer 115 are part of an illumination optics subsystem. Beam 114 illuminates a portion of wafer 115 including a measurement spot 116. A beam of collected light 117 is collected from measurement spot 116. Collected light 117 passes through a compensator 118 (e.g., a quarter waveplate compensator, phase retarder, etc.), collection optics 119 including collection pupil stop 120, a collection field stop 121, and an analyzer element 122. The beam of collected light 117 is incident on the surface of a detector 123. The elements between wafer 115 and detector 123 are part of a collection optics subsystem.

In one example, detector 123 is a photovoltaic detector. However, in general, other detector technologies may be contemplated (e.g., a position sensitive detector (PSD), an infrared detector, a charge coupled device (CCD), etc.). Detector 123 converts the collected light into electrical signals 125 indicative of the intensity of the collected light. Light collected from measurement spot 116 is projected onto detector 123 over detected spot 124. In this sense, measurement spot 116 includes locations on the wafer that originate the portion of collected light that is ultimately projected onto the surface of detector 123.

Computing system 130 receives measured signals 125 and performs model-based measurements of parameters of interest of the metrology target based on the measured signals 125.

As depicted in FIG. 1, the beam of illumination light 114 is provided to the surface of wafer 115 at an oblique angle. In general, illumination light may be provided to the surface of wafer 115 at any oblique angle or number of oblique angles.

The beam of illumination light 114 is narrowband illumination light. In one example, the narrowband illumination light has a center wavelength of approximately 632.8 nanometers with an extremely narrow band (e.g., sub-nanometer range of wavelengths). In some examples, the emission spectrum of the narrowband light source is generated by a laser (e.g., a Helium-Neon laser). However, in general, any suitable narrow band illumination source may be contemplated within the scope of this patent document.

As depicted in FIG. 1, the Z-axis is oriented normal to the surface of wafer 115. The X and Y axes are coplanar with the surface of wafer 115, and thus perpendicular to the Z-axis. The chief ray 126 of the beam of illumination light 114 and the chief ray 127 of the beam of collected light 117 define a plane of incidence that is perpendicular to the XY plane. The beam of illumination light 114 is incident on the surface of wafer 115 at an angle of incidence, AOI, with respect to the Z-axis and lies within the plane of incidence, X'Z. The plane of incidence is oriented with respect to a coordinate frame, XY, fixed to wafer 116 at an azimuth angle, Az.

The geometric projection of a beam of illumination light onto the surface of a specimen at an oblique angle results in an elongation of the illumination beam cross-section in the direction aligned with the plane of incidence. By way of non-limiting example, a circular beam of illumination light projected on the wafer surface results in an illumination area that is elliptical in shape. Thus, in general, oblique illumination of a surface results in a projected illumination area that is elongated relative to the illumination cross section, and the direction of elongation is aligned with the plane of incidence. Moreover, the magnitude of the elongation increases as the angle of incidence increases. More specifically, the beam shape is inversely proportional to the cosine of the angle of incidence in the direction of the plane of incidence in the absence of diffraction and aberration effects.

Figure 2:
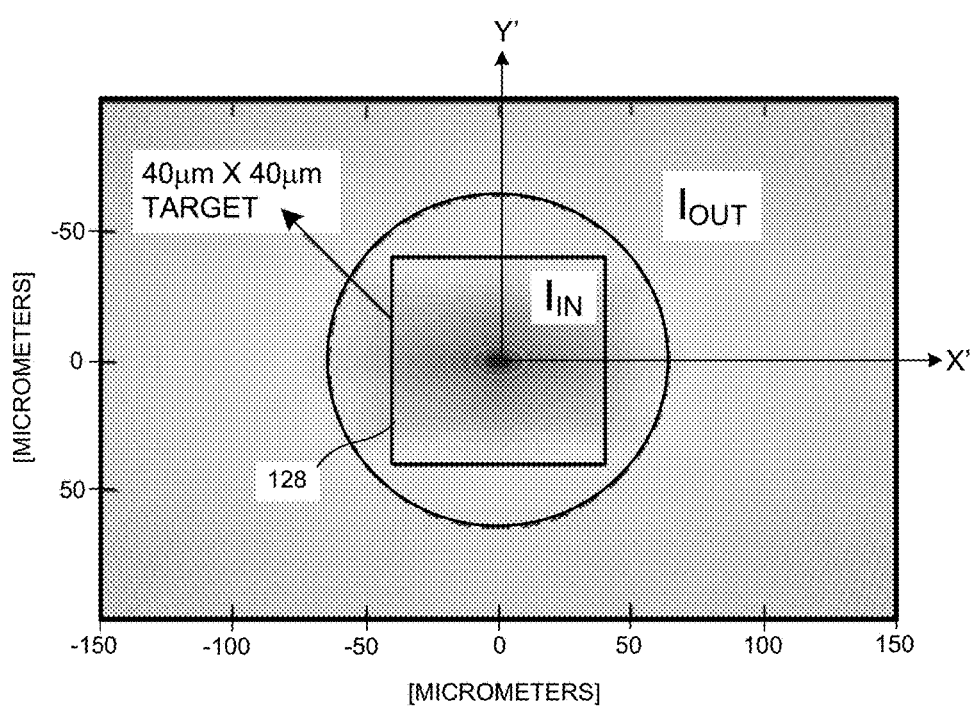
FIG. 2 depicts a plot illustrating a simulation of the irradiance at the wafer plane in and around an illuminated metrology target.

FIG. 2 depicts a plot illustrating a simulation of the irradiance at the wafer plane centered about the middle of a metrology target 128 disposed on wafer 115. The incoming beam (e.g., a beam having Gaussian beam profile) illuminates the metrology target as well as areas surrounding metrology target. The boundaries of metrology target 128 (e.g., thin film pad) are illustrated. Irradiance that exists within the boundaries of metrology target 128 is labeled, $I_{in}$. Irradiance that exists outside the boundaries of metrology target 128 is labeled, $I_{out}$. As depicted in FIG. 2, the metrology target is square in shape having dimensions of 40 micrometers by 40 micrometers.

Similar to coronographic measurements in astronomical applications, the illumination light diffracts around the edges of the target. In some examples, the diffraction of illumination light at the target edge generates an undesirable halo in the projected image. The exact physical realization of the halo effect depends on the projected shape and size of the target. But, this diffracted light interferes with light originating from inside the metrology target area, and thus causes errors in the measurement of thickness.

In one aspect, a round shaped aperture is located in the beam of collected light near the pupil plane of the collection optics of SWE system 100. In the embodiment depicted in FIG. 1, collection optics 119 includes pupil stop 120 integrated with the collection objective. In the depicted embodiment, pupil stop 120 includes a non-transparent structure having a round-shaped aperture though which light can freely pass.

In a preferred embodiment, pupil stop 120 is located in the pupil plane of the collection optics. At this location there is maximum separation between light originating from within the metrology target, and light originating from outside the metrology target. In this location, pupil stop 120 is most effective at blocking undesired light. In addition, the collected beam of light has maximum extent at this location.

The total irradiance, I(r), at any plane along the optical axis of the collected light (i.e., optical z-axis) can be expressed by equation (1), $$I(r) = I_{in} + I_{out} + I_{int} \quad (1)$$

where $I_{in}$, is the irradiance that originates from light within the metrology target, $I_{out}$, is the irradiance that originates from light outside of the metrology target, and $I_{int}$, is the irradiance that originates from interference between light within the metrology target and light outside the metrology target as expressed by equation (2), $$I_{int} = 2\sqrt{I_{in}I_{out}} |\hat{a}_{in} \cdot \hat{a}_{out}| \cos(k_\Delta \cdot r + \varphi_\Delta + \varphi_p) \quad (2)$$

where $\hat{a} = a_x \hat{X} + a_y \hat{X} + a_z \hat{X}$ is the polarization vector of each wave with $\|\hat{a}\| = 1$, $\phi_\Delta$ is the phase difference between the components and $\phi_p = \arg(\hat{a}_{in} \cdot \hat{a}_{out})$. Assuming the worst case scenario, the polarization vectors associated with light inside the metrology target and the polarization vectors associated with light outside the metrology target are set to be equal, $\hat{a}_{in} = \hat{a}_{out}$.

Equation (3) expresses a signal to contamination metric (SCR), that defines a ratio of desired signals (i.e., signals originating from within the metrology target area) to contamination signals (e.g., signals originating from outside the metrology target area and interference signals) as a function of location along the optical axis of the collected light (i.e., optical z-axis).

$$SCR(z) = \frac{I_m}{I_{out} + I_{int}} \quad (3)$$

A search is performed to identify the location of the highest value of SCR along the optical path. In some embodiments, the location of the highest value of SCR is located where there is maximum separation between desired signals and contamination signals where a physical obscuration device, e.g., an aperture, is most effective at blocking contamination signals with minimal blockage of desired signals. In one example, only interference is included as a source of undesired signal contamination. In accordance with Babinet's Principle, the diffracted field from the aperture is decomposed into segments and propagated separately for modeling purposes.

Figure 3:
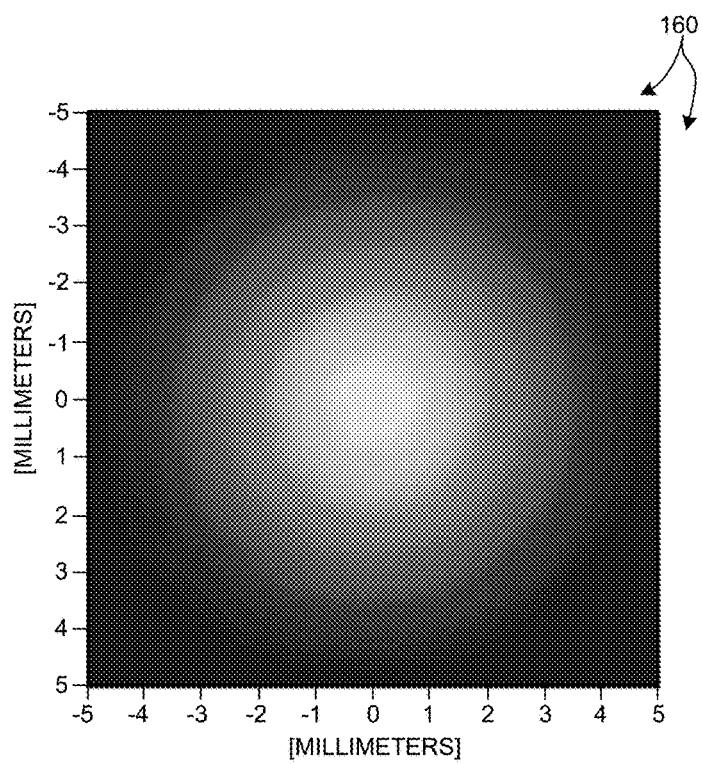
FIG. 3 depicts a plot 160 illustrating a simulation of the irradiance distribution of the collected beam at a collection pupil plane due to light originating from inside the metrology target.

FIG. 3 depicts a plot 160 illustrating a simulation of the irradiance distribution of the collected beam at the collection pupil plane due to light originating from inside the metrology target.

Figure 4:
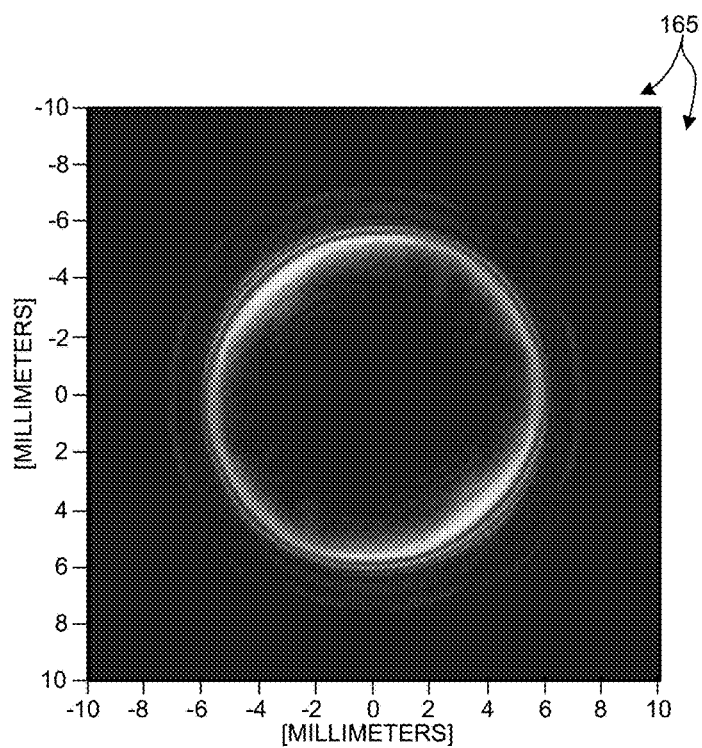
FIG. 4 depicts a plot 165 illustrating a simulation of the irradiance distribution of the collected beam at a collection pupil plane due to light originating from outside the metrology target.

FIG. 4 depicts a plot 165 illustrating a simulation of the irradiance distribution of the collected beam at the collection pupil plane due to light originating from outside the metrology target.

The signals represented in FIG. 3 are desirable and should be detected, while the signals represented in FIG. 4 are undesireable and should be removed before detection.

The light diffracted from the metrology target 128 as imaged in the pupil plane is redistributed and concentrated near the edges of the pupil, as illustrated in FIG. 4. Thus, a high SCR is obtained at this location. The undesired signals concentrated at the periphery of the beam are removed by a pupil stop with a relatively large opening (e.g., on the order of millimeters). The irradiance distribution of the collected light source is most spatially concentrated at the wafer plane. Hence, edge diffraction effects are most prominent for relatively small metrology targets. Thus, the use of a pupil stop to mitigate these effects is most effective for relatively small metrology targets.

Figure 5:
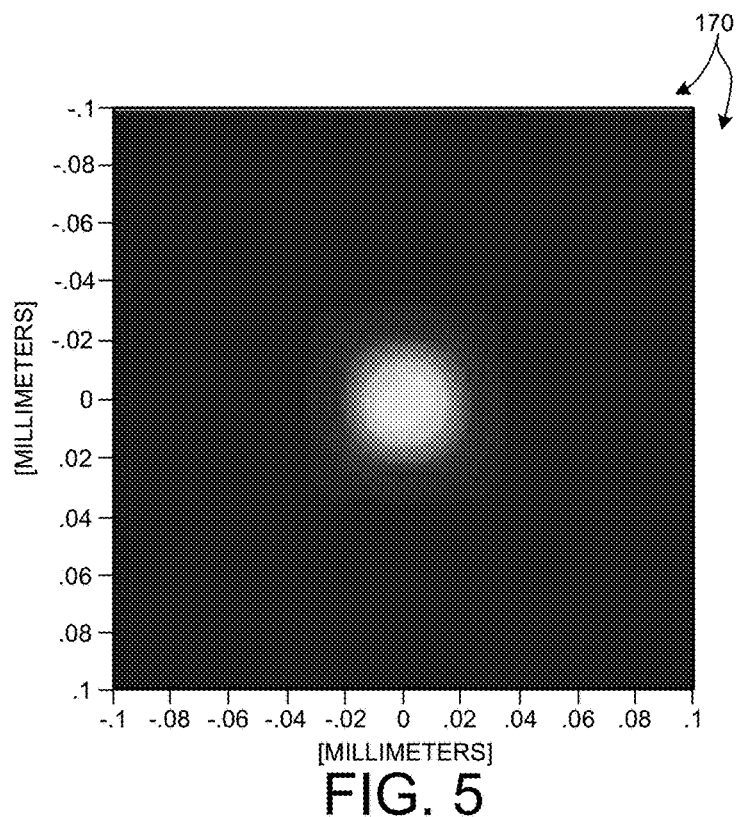
FIG. 5 depicts a plot 170 illustrating a simulation of the irradiance distribution of the collected beam at a collection image plane due to light originating from inside the metrology target.

FIG. 5 depicts a plot 170 illustrating a simulation of the irradiance distribution of the collected beam at the collection image plane due to light originating from inside the metrology target.

Figure 6:
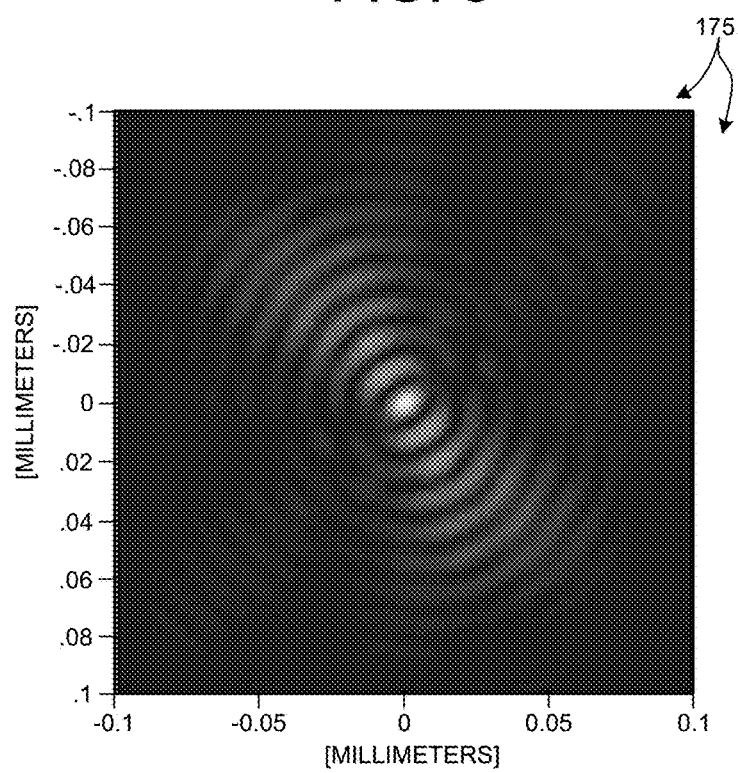
FIG. 6 depicts a plot 175 illustrating a simulation of the irradiance distribution of the collected beam at a collection image plane due to light originating from outside the metrology target.

FIG. 6 depicts a plot 175 illustrating a simulation of the irradiance distribution of the collected beam at the collection image plane due to light originating from outside the metrology target.

Figure 7:
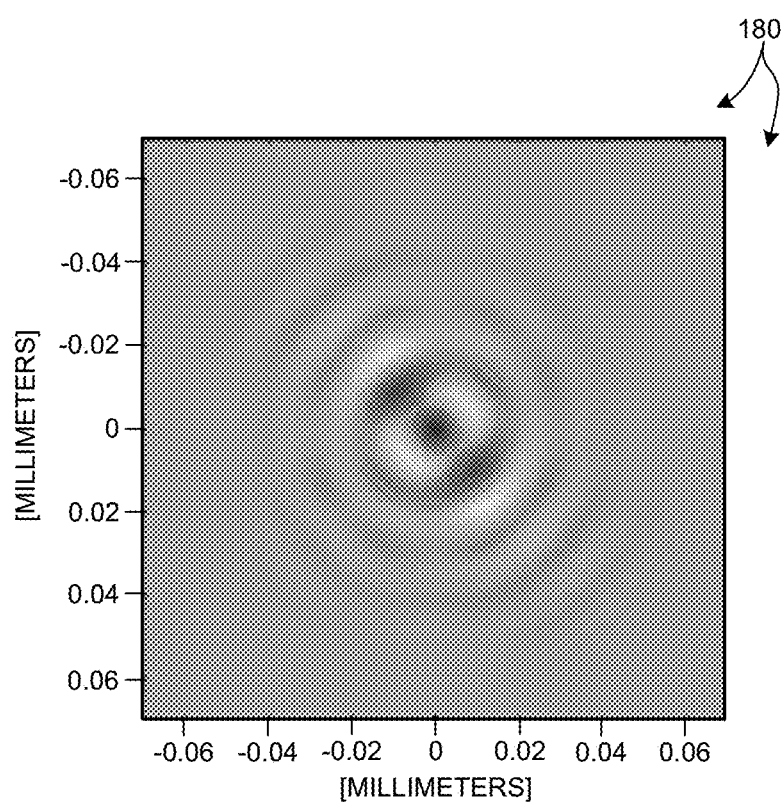
FIG. 7 depicts a plot 180 illustrating a simulation of the irradiance distribution of the collected beam at a collection image plane due to interference between light originating from inside the metrology target and light originating from outside the metrology target.

FIG. 7 depicts a plot 180 illustrating a simulation of the irradiance distribution of the collected beam at the collection image plane due to interference between light originating from inside the metrology target and light originating from outside the metrology target.

FIG. 5 depicts an image of the desired light that should be detected. However, as depicted in FIGS. 6 and 7, undesired light due to edge diffraction and interference is not spatially separated from the desired light in a simple manner at the image plane of the collection optics. Thus, a low SCR is obtained at this location. For this reason, an aperture located at the image plane is not effective at blocking undesirable light signals induced by diffraction at the edges of a metrology target.

In another aspect, a rectangular shaped field stop is included in the collection optical path near an image plane of the collection optics of a SWE system. In the embodiment depicted in FIG. 1, field stop 121 is located in the image plane before analyzer 122. In the depicted embodiment, field stop 121 includes a non-transparent plate having a rectangular-shaped aperture though which light can freely pass.

A field stop located in the collection optical path at an intermediate image plane prevents light outside the field of view from reaching the detector. In one example, the field stop, removes stray light arising from interactions between the beam of collected light and opto-mechanical elements in the beam path. These interactions typically manifest themselves as a relatively large radius ring around the beam of collected light. This particular manifestation is due to the symmetrical cylindrical housings of the optical elements in the beam path.

Stray light arising from interactions between the beam of collected light and opto-mechanical elements in the beam path is especially prevalent in the measurement of larger targets. In one example, a projection of the image of the target on an image plane of the collection objective is determined based on the measurement target size. The size of the field stop aperture is calculated based on the magnification of the collection objective.

Figure 8:
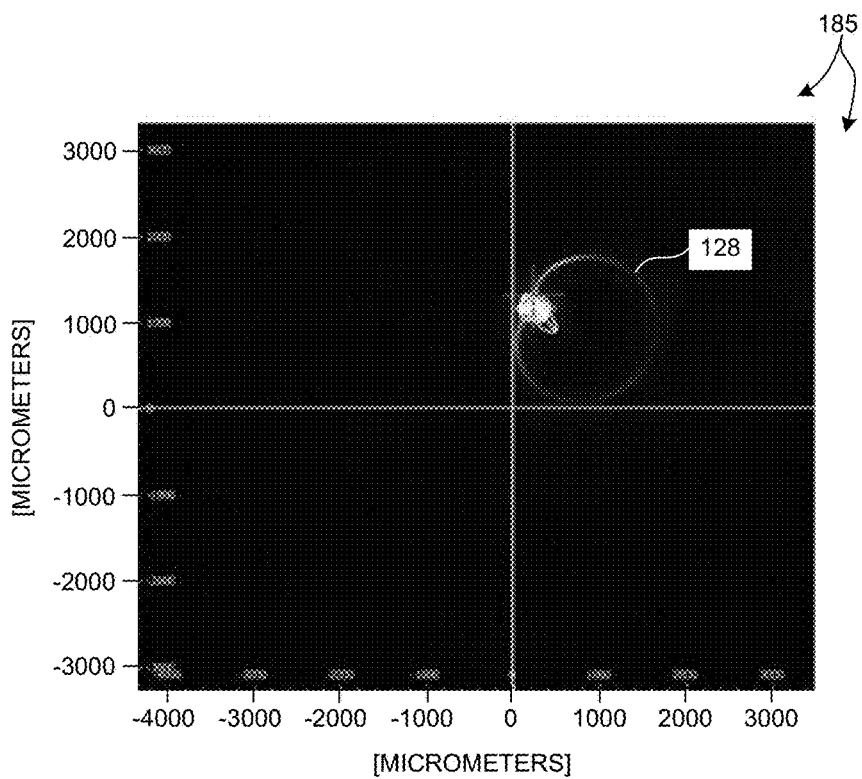
FIG. 8 depicts a plot 185 illustrating a measurement of the irradiance distribution at a conjugate plane to the collection objective before filtering.

FIG. 8 depicts a plot 185 illustrating a measurement of an illumination beam at a conjugate plane to the collection objective without filtering. As illustrated in FIG. 8, stray light appears in the image as a ring 128 around the beam of light.

Figure 9:
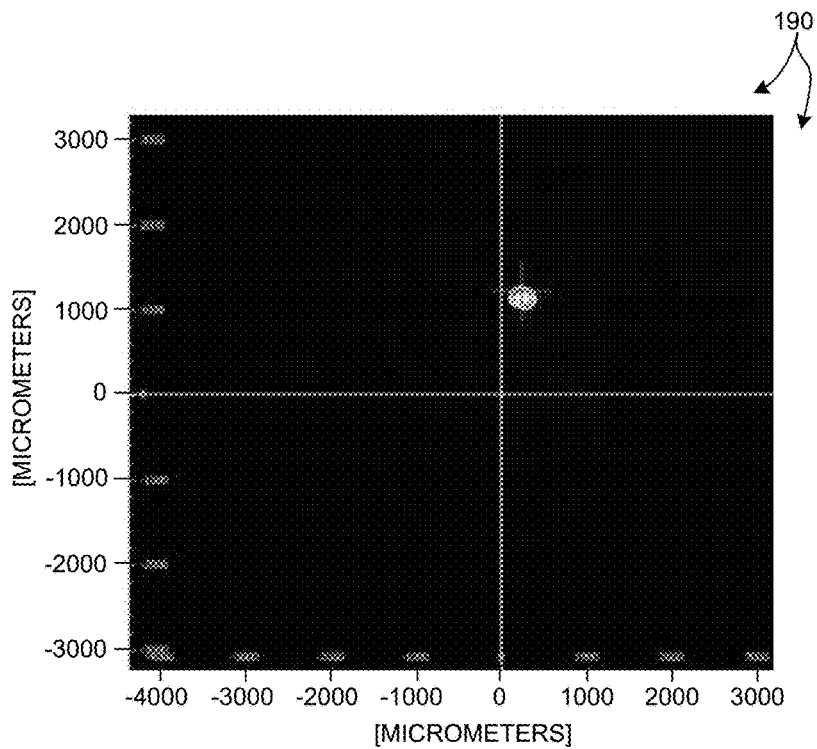
FIG. 9 depicts a plot 190 illustrating a measurement of the irradiance distribution at a conjugate plane to the collection objective after filtering.

FIG. 9 depicts a plot 190 illustrating a of an illumination beam at a conjugate plane to the collection objective for the case where an appropriately sized field stop is located in the collection optical path as described herein. As illustrated in FIG. 9, the field stop filters out the unwanted light reflected from outside the metrology target.

In another aspect, a linear polarizer located in the illumination path of a SWE system between the illumination source and any elliptical polarizer element includes a thin, high extinction ratio, nanoparticle based polarizer element. In the embodiment depicted in FIG. 1, a thin, nanoparticle based polarizer element 111 is located in the illumination path after the illumination source 110, but before elliptical polarizer 113. As such, polarizer element 111 is sometimes referred to as an input beam polarizer employed to condition the input beam, rather than the elliptical polarizer employed to impart a reference polarization onto the illumination beam for measurement purposes. In the embodiment depicted in FIG. 1, the thin, nanoparticle based polarizer element 111 absorbs light that is polarized perpendicular to the transmission axis. Polarization is generated in the thin, nanoparticle based polarizer element 111 by spherical ellipsoid nanoparticles embedded in sodium-silicate glass. Exemplary thin, nanoparticle based polarizers are available from Thorlabs, Inc., Newton, N.J. (USA).

Thin, nanoparticle based polarizers provide a similar extinction ratio as a traditional Glan-Thompson (GT) polarizer and a significantly higher damage threshold compared to conventional polymer-based components. In some embodiments, the thin, nanoparticle based polarizer element 111 is approximately 200 micrometers thick, while a comparable GT polarizer is approximately 10 millimeters thick. The thin polarizer provides better aberration control and the index of refraction of the thin, nanoparticle based polarizer does not depend on angle of incidence. This leads to a significant reduction in astigmatism in the optical system, and thus reduced spot size capability. In contrast, a traditional GT polarizer configuration separates beam polarizations by refraction, but the extraordinary ray refraction index is angle dependent while the ordinary wave index is constant. This results in aberrations and a reduction in beam quality.

Figure 10:
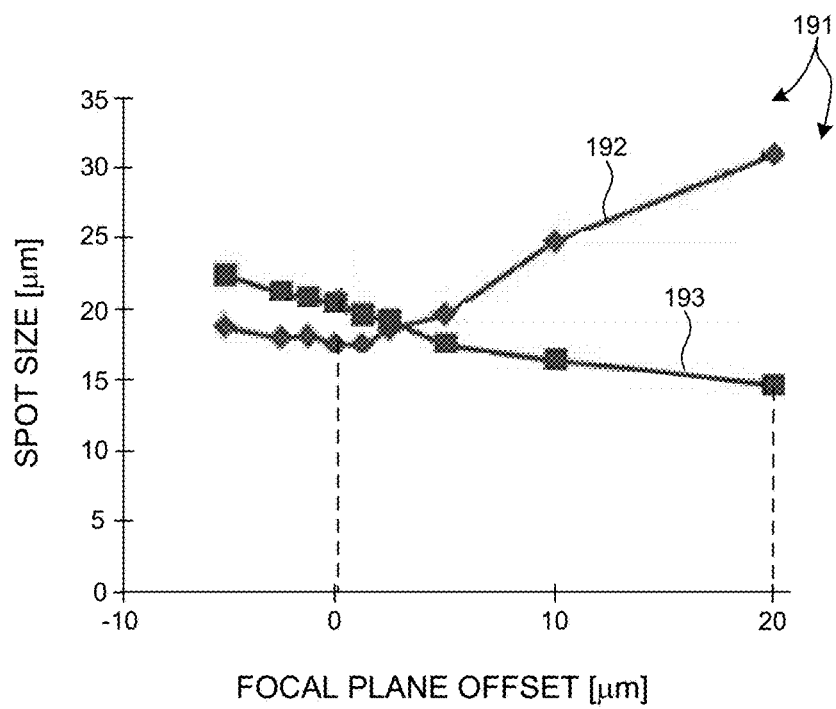
FIG. 10 depicts a plot 191 illustrative of measurement spot sizes obtained with different focal plane offset distances for a traditional SWE system.

FIG. 10 depicts a plot 191 illustrative of measurement spot sizes obtained with different focal plane offset distances for a traditional SWE system. Plotline 192 illustrates the measurement spot size at the wafer plane in the X'-direction depicted in FIG. 1 for various focal plane offset distances. Plotline 193 illustrates the measurement spot size at the wafer plane in the Y'-direction depicted in FIG. 1 for various focal plane offset distances. Plot 191 is generated based on experimental data collected from a SWE system employing a conventional GT polarizer. Due to astigmatism effects, the minimum spot sizes measured in the X'-direction and the Y'-direction reach their minimum sizes at different focal plane offsets. Thus, it is not possible to select a focal plane offset that minimizes the measurement spot size in both directions.

Figure 11:
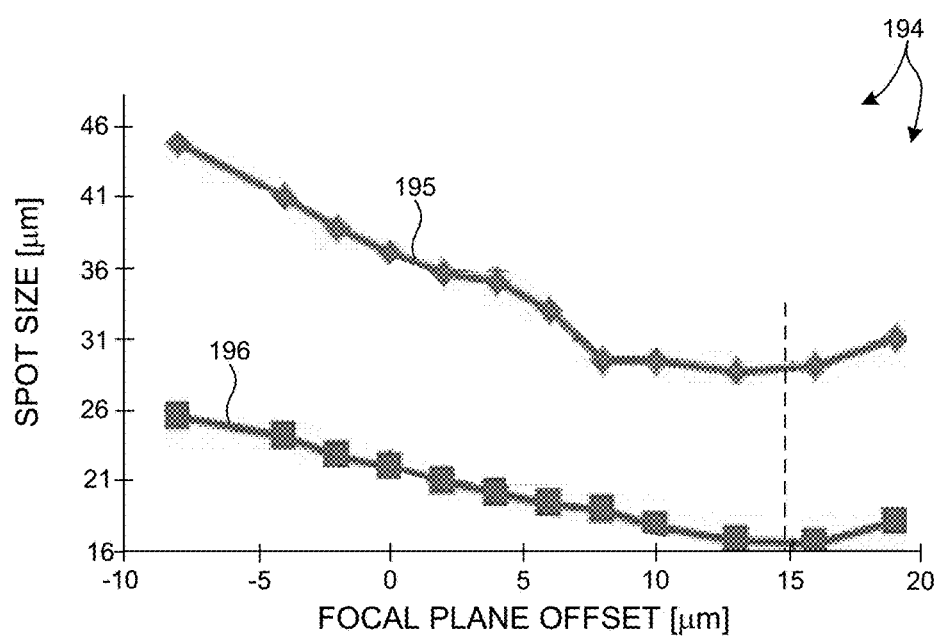
FIG. 11 depicts a plot 194 illustrative of measurement spot sizes obtained with different focal plane offset distances for a SWE system incorporating a nanoparticle based input beam polarizer.

FIG. 11 depicts a plot 194 illustrative of measurement spot sizes obtained with different focal plane offset distances for a SWE system incorporating a nanoparticle based input beam polarizer, such as SWE system 100. Plotline 195 illustrates the measurement spot size at the wafer plane in the X'-direction depicted in FIG. 1 for various focal plane offset distances. Plotline 196 illustrates the measurement spot size at the wafer plane in the Y'-direction depicted in FIG. 1 for various focal plane offset distances. In this scenario, the minimum spot sizes measured in the X'-direction and the Y'-direction reach their minimum sizes at nearly the same focal plane offset (i.e., focal plane offset of approximately 15 micrometers as depicted in FIG. 11). Thus, it is possible to select a focal plane offset that minimizes the measurement spot size in both directions.

Figure 12:
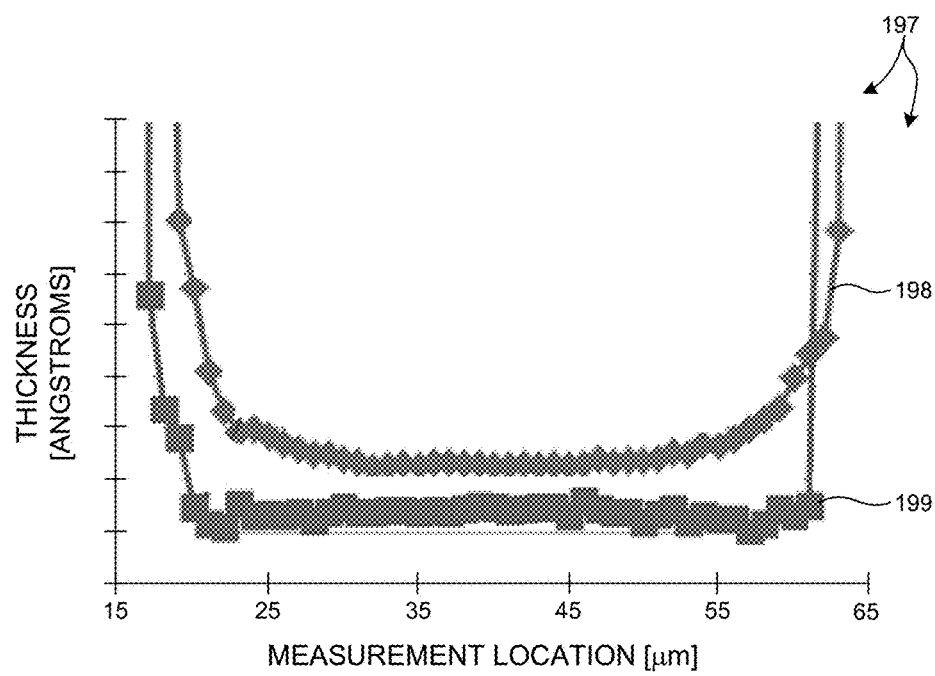
FIG. 12 depicts a plot 197 illustrative of SWE measurement results of a metrology target having a rectangular, well-shaped structure.

By way of example, FIG. 12 illustrates improvements (i.e., a reduction) in effective measurement spot size by employing field and pupil stops as described herein. FIG. 12 depicts a plot 197 illustrative of SWE measurement results of a metrology target having a rectangular, well-shaped structure. The illumination spot was scanned across the target. In the example provided, a film thickness characterizing the target was measured by identifying a film thickness parameter that gave the best fit to measured SWE signals. The film thickness variation is expected to stay within a prescribed range while the illumination beam remains within the well-shaped structure. Hence, it is presumed that an undesireable interaction of the illumination beam with the edges of the target area is occurring when the measurement results move outside of this range.

Plotline 198 depicts measurements performed with a traditional SWE system that lacks the pupil stop, field stop, and thin nanoparticle based input beam polarizer as described herein. In the illustrated example, the measurement is stable over a linear scan of approximately 20 micrometers (i.e., as center of measurement beam is scanned between 30 micrometers and 50 micrometers). Beyond this limited range, the beam begins to interact with the edges of the well-shaped target and the measured thickness begins to increase.

Plotline 199 depicts measurements performed with a SWE system that includes the pupil stop, field stop, and thin nanoparticle based input beam polarizer as described herein. In the illustrated example, the measurement is stable over a linear scan of approximately 40 micrometers (i.e., as center of measurement beam is scanned between 20 micrometers and 60 micrometers). Beyond this range, the beam begins to interact with the edges of the well-shaped target and the measured thickness begins to increase. Note that the effective measurement spot size is smaller for the SWE system including the pupil stop, field stop, and thin, nanoparticle based input beam polarizer because the range of linear scan is significantly larger before edge effects begin to impact the measurement.

Measurements by a SWE system that includes the pupil stop, field stop, and thin nanoparticle based input beam polarizer as described herein demonstrate tool-to-tool matching of film thickness measurements down to 0.02 Angstroms for a 40 um×40 um measurement target. Similar measurements performed on a SWE system that does not include the pupil stop, field stop, and thin nanoparticle based input beam polarizer as described herein demonstrate tool-to-tool matching of film thickness measurements greater than 0.2 for the same 40 um×40 um measurement target.

In some embodiments, SWE system 100 is configured as a discrete measurement polarizer and rotating compensator system. In these embodiments, measurements are performed at discrete polarizer angles with a continuously rotating compensator (e.g., compensator 118 depicted in FIG. 1) for one or more azimuth angles and angles of incidence. In some embodiments, polarizer 113 includes a rotatable polarizer element and computing system 130 communicates a command signal 141 indicative of a desired polarization state to polarizer 113. In response, polarizer 113 rotates and stops at the desired polarization state. In this manner, SWE system 100 is configured to stop at a fixed polarization angle.

In some embodiments, SWE system 100 is configured as a rotating polarizer system. In these embodiments, measurements are performed while the polarization state is continuously changing for one or more azimuth angles and angles of incidence. In some embodiments, polarizer 113 includes a rotatable polarizer element and computing system 130 communicates a command signal 141 indicative of a desired rate of change of polarization state to polarizer 113. In response, polarizer 113 rotates at a desired angular velocity.

In some embodiments, SWE system 100 is configured as a rotating polarizer and rotating compensator system. In these embodiments, measurements are performed with a continuously rotating polarizer (e.g., polarizer 113 depicted in FIG. 1) and a continuously rotating compensator (e.g., compensator 118 depicted in FIG. 1) for one or more azimuth angles and angles of incidence. In some embodiments, compensator 118 includes a rotatable polarizer element and computing system 130 communicates a command signal 145 indicative of a desired rate of change of polarization state to compensator 118. In response, compensator 118 rotates at the desired angular velocity.

In a further aspect, SWE system 100 also includes a selective analyzer angle. Similarly, computing system 130 communicates a command signal 142 indicative of a desired analyzer angle to the selective analyzer 122.

Regardless of polarization state, in some embodiments, SWE system 100 is also configured to select ranges of AOI and Az for measurement.

Figure 13:
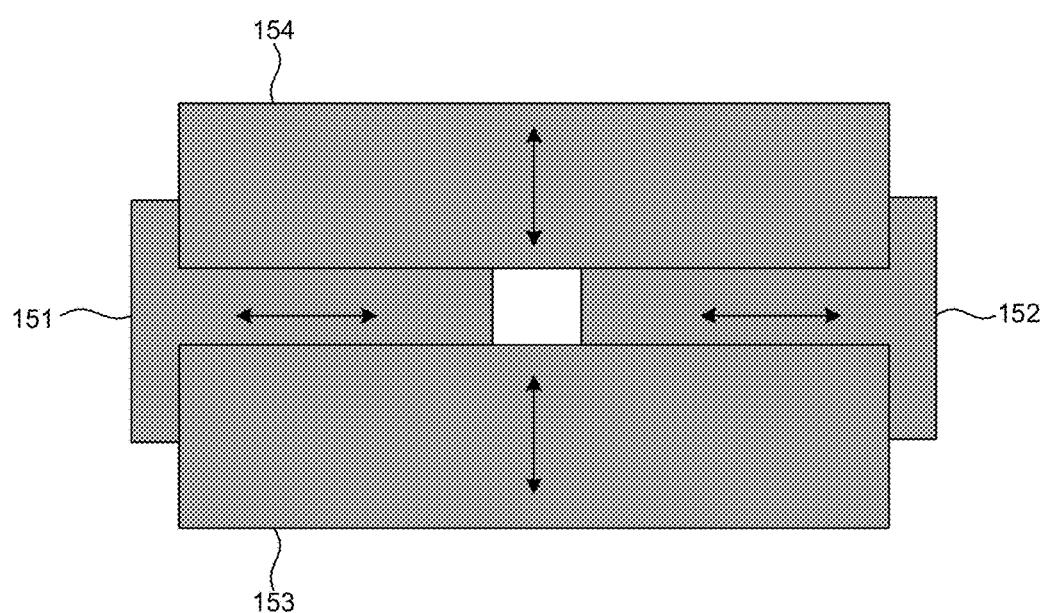
FIG. 13 depicts an embodiment of a field stop including four moveable, absorptive panels configured to move relative to one another to achieve a rectangular shaped aperture of a desired dimension and location.

In some embodiments field stop 121 is adjusted to achieve the desired signal rejection. As depicted in FIG. 1, computing system 130 communicates a command signal 143 indicative of a desired aperture size to field stop 121. In response, field stop 121 adjusts to the desired aperture size. In some embodiments, field stop 121 includes active elements such as moveable slits, knife edges, MEMS based mirror elements, etc., that are configured to adjust the aperture size. FIG. 13 depicts an embodiment of a field stop 121 including four moveable, absorptive panels 151-154 configured to move relative to one another to achieve a rectangular shaped aperture of a desired dimension and location.

In some embodiments the pupil stop 120 is adjusted to achieve the desired signal rejection. As depicted in FIG. 1, computing system 130 communicates a command signal 144 indicative of a desired pupil stop aperture size to pupil stop 120. In response, pupil stop 120 adjusts to the desired aperture size. In these embodiments, pupil stop 120 includes active elements such as moveable shutter elements, knife edges, MEMS based mirror elements, etc., that are configured to adjust the aperture of pupil stop 120.

In some embodiments, the azimuth angle is selected by rotating the metrology target with respect to the plane of incidence of the metrology system. For example, SWE system 100 may include a rotary stage supporting specimen 115. In these embodiments, computing system 130 communicates a command signal to the rotary stage to rotate specimen 115 with respect to the optics system (e.g., rotation about the z-axis depicted in FIG. 1) to achieve the desired azimuth angle.

In a further aspect, the dimensions of the apertures of the field stop, pupil stop, or both are adjusted to increase measurement sensitivity to structure specific features, such as film thickness, by limiting light transmission. By limiting light transmission, light associated with light originating outside the metrology target at the wafer plane, interference light generated by the interaction between light originating inside the metrology target and light originating outside the metrology target, and stray light reflected into the collected beam is absorbed, or otherwise redirected away from the detector. In this manner, light rays that are most sensitive to changes in the parameter of interest are detected.

Figure 14:
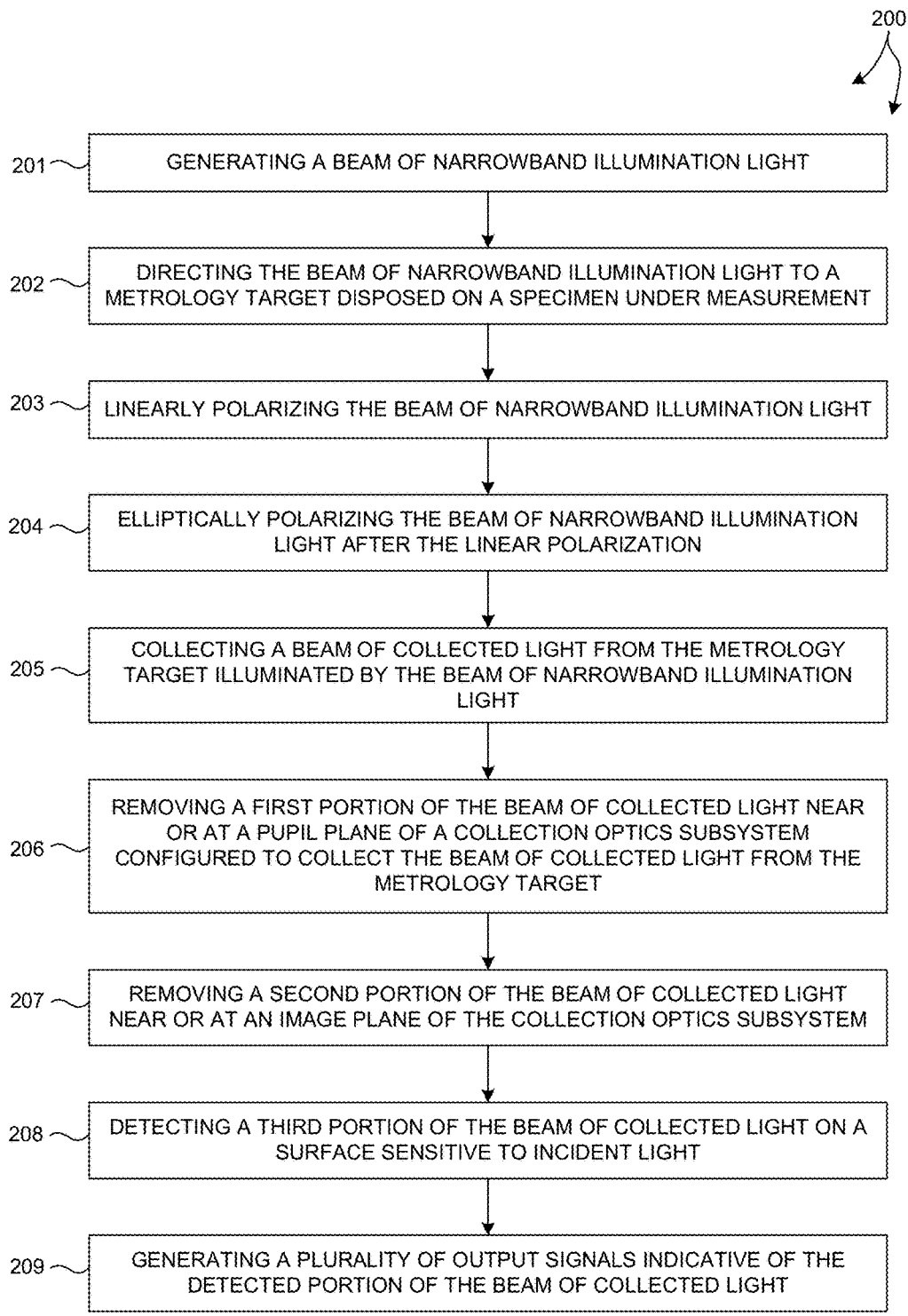
FIG. 14 illustrates a method 200 of performing SWE measurements in at least one novel aspect.

FIG. 14 illustrates a method 200 of performing SWE measurements in at least one novel aspect. Method 200 is suitable for implementation by a metrology system such as SWE system 100 illustrated in FIG. 1 of the present invention. In one aspect, it is recognized that data processing blocks of method 200 may be carried out via a pre-programmed algorithm executed by one or more processors of computing system 130, or any other general purpose computing system. It is recognized herein that the particular structural aspects of SWE system 100 do not represent limitations and should be interpreted as illustrative only.

In block 201, a beam of narrowband illumination light is generated by an illumination source.

In block 202, the beam of narrowband illumination light is directed by an illumination optics subsystem to a metrology target disposed on a specimen (e.g., a semiconductor wafer) under measurement.

In block 203, the beam of narrowband illumination light is linearly polarized by a linear polarizer. In some embodiments, the linear polarizer is a thin, nanoparticle based polarizer.

After linear polarization, in block 204, the beam of narrowband illumination light is elliptically polarized.

In block 205, a beam of collected light is collected from the metrology target illuminated by the beam of narrowband illumination light.

In block 206, a first portion of the beam of collected light is removed from the remainder of the beam of collected light at or near a pupil plane of a collection optics subsystem configured to collect the beam of collected light from the metrology target. In some embodiments, the first portion of the beam of collected light is removed by an aperture configured to absorb or redirect the removed light;

In block 207, a second portion of the beam of collected light is removed from the remainder of the beam of collected light at or near an image plane of the collection optics subsystem. In some embodiments, the second portion of the beam of collected light is removed by an aperture configured to absorb or redirect the removed light.

In block 208, a third portion of the beam of collected light is detected on a surface of a detector sensitive to incident light.

In block 209, a plurality of output signals indicative of the detected portion of the beam of collected light are generated by the detector.

In general, the methods and systems for control of signal contamination described herein are not limited to application in single wavelength ellipsometer systems, and may be implemented in any partial coherent metrology system, including spectroscopic ellipsometry systems, etc.

In a further embodiment, system 100 includes one or more computing systems 130 employed to perform measurements of actual device structures based on measurement data collected in accordance with the methods described herein. The one or more computing systems 130 may be communicatively coupled to a detector (e.g., detector 123). In one aspect, the one or more computing systems 130 are configured to receive measurement data 125 associated with measurements of the structure of specimen 115.

It should be recognized that one or more steps described throughout the present disclosure may be carried out by a single computer system 130 or, alternatively, a multiple computer system 130. Moreover, different subsystems of the system 100, such as the detector 123, may include a computer system suitable for carrying out at least a portion of the steps described herein. Therefore, the aforementioned description should not be interpreted as a limitation on the present invention but merely an illustration.

In addition, the computer system 130 may be communicatively coupled to the detector 123 in any manner known in the art. For example, the one or more computing systems 130 may be coupled to computing systems associated with the detector 123. In another example, the detector 123 may be controlled directly by a single computer system coupled to computer system 130.

The computer system 130 of the SWE system 100 may be configured to receive and/or acquire data or information from the subsystems of the system (e.g., detector 123 and the like) by a transmission medium that may include wireline and/or wireless portions. In this manner, the transmission medium may serve as a data link between the computer system 130 and other subsystems of the system 100.

Computer system 130 of SWE system 100 may be configured to receive and/or acquire data or information (e.g., measurement results, modeling inputs, modeling results, reference measurement results, etc.) from other systems by a transmission medium that may include wireline and/or wireless portions. In this manner, the transmission medium may serve as a data link between the computer system 130 and other systems (e.g., memory on-board SWE system 100, external memory, or other external systems). For example, the computing system 130 may be configured to receive measurement data from a storage medium (i.e., memory 132 or an external memory) via a data link. For instance, intensity measurement results obtained using detector 123 may be stored in a permanent or semi-permanent memory device (e.g., memory 132 or an external memory). In this regard, the measurement results may be imported from on-board memory or from an external memory system. Moreover, the computer system 130 may send data to other systems via a transmission medium. For instance, a measurement model or an actual device parameter value determined by computer system 130 may be communicated and stored in an external memory. In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 1, program instructions 134 stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

In some examples, the measurement models are implemented as an element of a SpectraShape® optical critical-dimension metrology system available from KLA-Tencor Corporation, Milpitas, Calif., USA. In this manner, the model is created and ready for use immediately after the measurement signals are collected by the system.

In some other examples, the measurement models are implemented off-line, for example, by a computing system implementing AcuShape® software available from KLA-Tencor Corporation, Milpitas, Calif., USA. The resulting, trained model may be incorporated as an element of an AcuShape® library that is accessible by a metrology system performing measurements.

In yet another aspect, the measurement model results described herein can be used to provide active feedback to a process tool (e.g., lithography tool, etch tool, deposition tool, etc.). For example, values of measured parameters determined based on measurement methods described herein can be communicated to a lithography tool to adjust the lithography system to achieve a desired output. In a similar way etch parameters (e.g., etch time, diffusivity, etc.) or deposition parameters (e.g., time, concentration, etc.) may be included in a measurement model to provide active feedback to etch tools or deposition tools, respectively. In some example, corrections to process parameters determined based on measured device parameter values and a trained measurement model may be communicated to a lithography tool, etch tool, or deposition tool.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including measurement applications such as critical dimension metrology, overlay metrology, focus/dosage metrology, and composition metrology. However, such terms of art do not limit the scope of the term "metrology system" as described herein. In addition, the SWE system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the methods described herein.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A metrology system, comprising:
    a narrowband illumination source configured to generate a beam of illumination light;
    an illumination optics subsystem configured to direct the beam of illumination light from the illumination source to a metrology target disposed on a specimen under measurement, the illumination optics subsystem including:
        a linear polarizer configured to receive the beam of illumination light generated by the narrowband illumination source and impart a linear polarization onto the beam of illumination light; and
        an elliptical polarizer configured to receive the beam of illumination light from the linear polarizer and impart an elliptical polarization onto the beam of illumination light;
    a detector having a planar, two-dimensional surface sensitive to incident light, wherein the detector is configured to generate a plurality of output signals indicative of a response of the specimen to the beam of illumination light; and
    a collection optics subsystem configured to collect a beam of collected light from the specimen and direct the beam of collected light to the surface of the detector, the collection optics subsystem including:
        an analyzer configured to receive the beam of collected light and impart a linear polarization onto the beam of collected light; and
        any of a field stop located in the beam of collected light near or at an image plane of the collection optics subsystem, and a pupil stop located in the beam of collected light at or near a pupil plane of the collection optics subsystem.

2. The metrology system of claim 1, wherein the linear polarizer includes a nanoparticle based polarizer element.

3. The metrology system of claim 1, wherein the field stop is a rectangular shaped aperture.

4. The metrology system of claim 1, wherein the pupil stop is a circular shaped aperture.

5. The metrology system of claim 1, wherein an area of an aperture of the pupil stop, an area of an aperture of the field stop, or both, are adjustable.

6. The metrology system of claim 1, wherein the pupil stop, the field stop, or both, are located in a collection optical path of the metrology system at one or more locations where a signal to contamination metric is maximized.

7. The metrology system of claim 1, further comprising:
    a computing system configured to communicate a first command signal to the pupil stop that causes the pupil stop to adjust the area of the aperture of the pupil stop to block light rays associated with light diffracted from edges of the metrology target, communicate a second command signal to the field stop that causes the field stop to adjust the area of the aperture of the field stop to block light rays associated with undesired light interactions with opto-mechanical elements of the collection optics subsystem, or communicate both the first and second command signals.

8. The metrology system of claim 1, wherein the elliptical polarizer is rotating at a predetermined angular velocity.

9. The metrology system of claim 1, wherein the metrology system is configured as a single wavelength ellipsometer.

10. The metrology system of claim 1, wherein the beam of illumination light is narrowband light having a range of wavelengths spanning less than one nanometer.

11. A method comprising:
    generating a beam of narrowband illumination light;
    directing the beam of narrowband illumination light to a metrology target disposed on a specimen under measurement;
    linearly polarizing the beam of narrowband illumination light;
    elliptically polarizing the beam of narrowband illumination light after the linear polarization;
    collecting a beam of collected light from the metrology target illuminated by the beam of narrowband illumination light;
    removing a first portion of the beam of collected light near or at a pupil plane of a collection optics subsystem configured to collect the beam of collected light from the metrology target;
    removing a second portion of the beam of collected light near or at an image plane of the collection optics subsystem;
    detecting a third portion of the beam of collected light on a surface sensitive to incident light; and
    generating a plurality of output signals indicative of the detected portion of the beam of collected light.

12. The method of claim 11, wherein the linearly polarizing of the beam of narrowband illumination light involves a nanoparticle based polarizer element.

13. The method of claim 11, wherein the removing of the first portion of the beam of collected light near or at the pupil plane of the collection optics subsystem involves a circular shaped aperture.

14. The method of claim 11, wherein the removing of the second portion of the beam of collected light near or at the image plane of the collection optics subsystem involves a rectangular shaped aperture.

15. The method of claim 11, further comprising:
    communicating a first command signal to a pupil stop that causes the pupil stop to adjust an area of an aperture of the pupil stop to block light rays associated with light diffracted from edges of the metrology target; and
    communicating a second command signal to a field stop that causes the field stop to adjust an area of an aperture of the field stop to block light rays associated with undesired light interactions with opto-mechanical elements of a collection optics subsystem.

16. A metrology system, comprising:
    a narrowband illumination source configured to generate a beam of illumination light;
    an illumination optics subsystem configured to direct the beam of illumination light from the illumination source to a metrology target disposed on a specimen under measurement, the illumination optics subsystem including:
- a linear polarizer configured to receive the beam of illumination light generated by the narrowband illumination source and impart a linear polarization onto the beam of illumination light; and
- an elliptical polarizer configured to receive the beam of illumination light from the linear polarizer and impart an elliptical polarization onto the beam of illumination light;

a detector having a planar, two-dimensional surface sensitive to incident light, wherein the detector is configured to generate a plurality of output signals indicative of a response of the specimen to the beam of illumination light;

a collection optics subsystem configured to collect a beam of collected light from the specimen and direct the beam of collected light to the surface of the detector, the collection optics subsystem including:
- an analyzer configured to receive the beam of collected light and impart a linear polarization onto the beam of collected light; and
- any of a field stop located in the beam of collected light near or at an image plane of the collection optics subsystem, and a pupil stop located in the beam of collected light at or near a pupil plane of the collection optics subsystem; and a non-transitory, computer-readable medium, comprising:
- code for causing a computing system to communicate a first command signal to the pupil stop that causes the pupil stop to adjust an area of an aperture of the pupil stop; and
- code for causing the computer system to communicate a second command signal to the field stop that causes the field stop to adjust an area of an aperture of the field stop.

17. The metrology system of claim 16, wherein the linear polarizer includes a nanoparticle based polarizer element.

18. The metrology system of claim 16, wherein the field stop is a rectangular shaped aperture, and wherein the pupil stop is a circular shaped aperture.

19. The metrology system of claim 16, wherein the metrology system is configured as a single wavelength ellipsometer.

20. The metrology system of claim 16, wherein the beam of illumination light is directed to the metrology target at a plurality of angles of incidence.

* * * * *